United States Patent [19]

Mitsuhashi et al.

[11] Patent Number: 4,520,212
[45] Date of Patent: May 28, 1985

[54] PROCESS FOR PRODUCING MYRCENOL

[75] Inventors: Shigeru Mitsuhashi; Hidenori Kumobayashi; Susumu Akutagawa, all of Kanagawa, Japan

[73] Assignee: Takasago Perfumery Co., Ltd., Tokyo, Japan

[21] Appl. No.: 563,810

[22] Filed: Dec. 21, 1983

[30] Foreign Application Priority Data

Dec. 27, 1982 [JP] Japan ................. 57-228479

[51] Int. Cl.³ .................. C07C 29/02; C07C 33/02
[52] U.S. Cl. .................................... 568/875
[58] Field of Search ........................ 568/875

[56] References Cited

U.S. PATENT DOCUMENTS 3,932,539 1/1976 Kane et al. ............. 568/875
4,107,219 8/1978 Murata et al. ........... 568/875

FOREIGN PATENT DOCUMENTS 0012224 5/1980 European Pat. Off. ........... 568/875
2720839 11/1977 Fed. Rep. of Germany ...... 568/875

*Primary Examiner*—Werren B. Lone
*Attorney, Agent, or Firm*—Oblon, Fisher, Spivak, McClelland & Maier

[57] ABSTRACT

Myrcenol is produced in an effecient, high yield and economical process by deaminating 7-hydroxygeranyl dialkylamine or 7-hydroxyneryl dialkylamine with a specific palladium-phosphine-cation complex catalyst represented by the formula

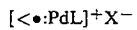

wherein $<\bullet$: represents $\eta$-allyl, L represents a tertiary phosphine, and X represents a counter anion.

10 Claims, No Drawings

PROCESS FOR PRODUCING MYRCENOL

BACKGROUND OF THE INVENTION

1. Field of the Invention

The present invention relates to a process for producing myrcenol. More particularly, it relates to a process for producing myrcenol by deaminating hydroxygeranyl dialkylamine or hydroxynerin dialkylamine with a palladium-phosphine-cation complex catalyst.

2. Description of the Prior Art

Myrcenol is a synthetic perfume having a floral limelike fragrance, and it is used as a perfume for soap. Myrcenol is also important as a raw material for synthetic perfumes such as dihydromyrcenol and tetrahydromyrcenol and (4-hydroxy-4-methylpentyl)-3-cyclohexene-1-carboxyaldehyde as an acrolein adduct.

In the past, myrcenol was obtained by treating myrcene with cold acetic acid-sulfuric acid mixture and decomposing the resulting myrcenylacetate. (U. J. Honlihan: J.A.C.S. 81 (1959) p. 4692) Recently, there has been proposed in U.S. Pat. No. 3,176,002 a new process for preparing myrcenol by reacting myrcene with sulfur dioxide to form a cyclic sulfone, hydrating the myrcene sulfone, and heating the resulting tertiary alcohol. There has also been proposed in U.S. Pat. No. 3,932,539 another process for preparing myrcenol by hydrochlorinating myrcene to form a mixture of linalyl chloride, neryl chloride, and geranyl chloride, changing the chloride into quarternary ammonium salt, hydrating the quarternary ammonium salt to give 3,7-dimethyl-7-hydroxy-2-octene-1-yl trimethylammonium chloride, converting this chloride to a hydroxide, and finally pyrolyzine the hydroxide.

These processes are unsatisfactory because of low yields, complex reaction steps, and difficulty in the recovery of amine. Thus there has been a demand for an efficient, high yield and an economical process for the preparation of myrcenol.

SUMMARY OF THE INVENTION

In accordance with the present invention it has been discovered that myrcenol may be prepared in a one step process and in high yield.

Further in accordance with the present invention, myrcenol may be prepared by deaminating 7-hydroxygeranyl dialkylamine or 7-hydroxyneryl dialkylamine with a specific palladium-phosphine-cation complex catalyst represented by the formula (I)

$$[<\bullet:PdL]^+X^- \qquad (I)$$

wherein $<\bullet$: represents $\eta$-allyl, L represents a tertiary phosphine, and X represents a counter anion.

These and other aspects of the invention will become clear to those skilled in the art upon the reading and understanding of the specification.

DETAILED DESCRIPTION OF THE INVENTION

It has previously been reported that the reaction to remove acetic acid or phenol from an allylic acetate compound or allylic phenyl ether compound in the presence of a palladium acetate-triphenylphosphine catalyst gives a corresponding diene compound in high yields. (Tsuji et al, *Tetrahedron Letters*, No. 24 (1978) pp. 2075-2078). This report describes that the deamination reaction of the allylic amine compound does not take place at all.

However, it has surprisingly been discovered that the specific palladium-phosphine-cation complex represented by the formula (I), above, effectively acts on the above-mentioned raw material compound to effect the deamination reaction.

The tertiary phosphine represented by L in the formula (I) includes two monodentate ligands represented by the formula (II) below or a bidentate ligand represented by the formula (III) below:

$$(R)_2-P-Y-P-(R)_2 \qquad (III)$$

wherein $R_1$, $R_2$, and $R_3$ are the same or different and represent lower alkyl groups, cycloalkyl groups, or aryl groups; $R_2$ and $R_3$ may jointly form a five-membered ring with the adjoining carbon atoms; R represents a lower alkyl group, cycloalkyl group, or aryl group; and Y represents $$-(CH_2)_2-, \ -(CH_2)_3-, \ -\overset{\underset{\displaystyle |}{CH_3}}{C}HCH_2-, \ -(CH_2)_4-,$$

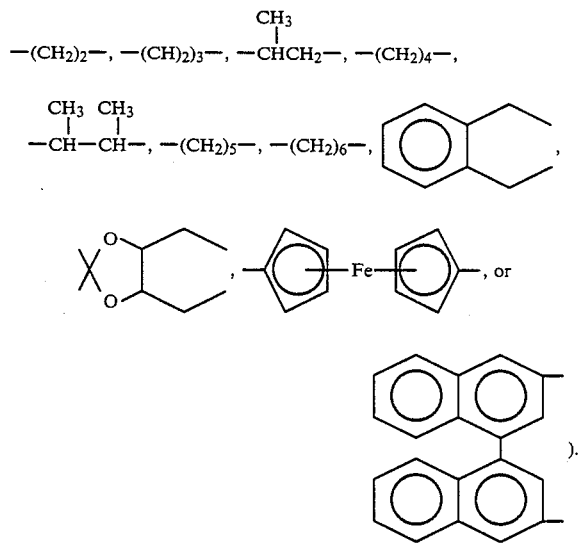

Illustratative of tertiary phosphines within the scope of the invention represented by the above formulas (II) and (III), the following species are mentioned:

| | |
|---|---|
| $(C_2H_5)_3P$ | Triethylphosphine |
| $Ph_2-P-(\overset{\underset{\displaystyle \|}{CH_3}}{C}H-CH_2)-P-Ph_2$ | 1,2-bis(diphenyl-phosphino)propane |
| $Ph_2-(CH_2)_4-P-Ph_2$ | 1,4-bis(diphenyl-phosphino)butane |
| $Ph_2-P-(\overset{\underset{\displaystyle \|}{CH_3}}{C}H-\overset{\underset{\displaystyle \|}{CH_3}}{C}H)-P-Ph_2$ | 2,3-bis(diphenyl-phosphino)butane |
| $Ph_2-P-(CH_2)_5-P-Ph_2$ | 1,5-bis(diphenyl-phosphino)pentane |
| $Ph_2-P-(CH_2)_6-P-Ph_2$ | 1,6-bis(diphenyl-phosphino)hexane |

| Structure | Name |
|---|---|
| (o-Tol)₂—P—(CH₂)₄—P—(o-Tol)₂ | Bis(1,4-di-o-tolyl-phosphino)butane |
| 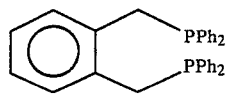 | Bis(α,α'-diphenyl-phosphino)ortho-xylylene |
| 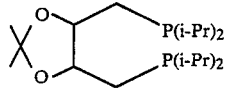 | 2,3-o-isopropylydene-2,3-dihydroxy-1,4-bis(diisopropyl phosphino)butane |
| 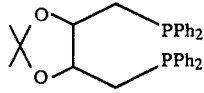 | 2,3-o-isopropylydene-2,3-dihydroxy-1,4-bis(dicyclohexyl-phosphino)butane |
| 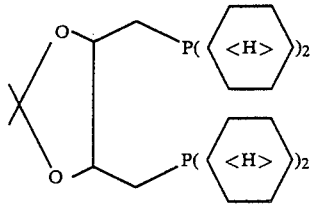 | 2,3-o-isopropylydene-2,3-dihydroxy-1,4-bis(dicyclohexyl-phosphino)butane |
| 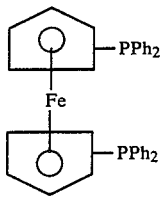 | 1,1'-bis(diphenyl-phosphino)-ferrocene |
| (C₃H₇)₃P | Tri-n-propylphosphine |
| (C₄H₉)₃P | Tributylphosphine |
| (C₈H₁₇)₃P | Trioctylphosphine |
| (C₆H₆)₃P | Triphenylphosphine |
| 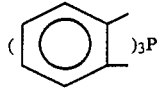 | Tri-o-tolylphosphine |
| 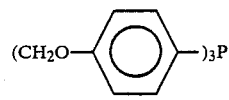 | Tri-p-methoxyphenyl-phosphine |
| 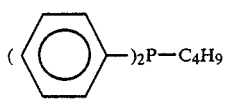 | Diphenylbutyl-phosphine |
| 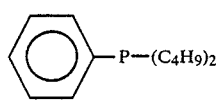 | Dibutyl phenyl phosphine |
| 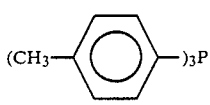 | Tri-p-tolylphosphine |
| 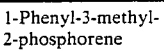 | 1-Phenyl-3-methyl-2-phosphorene |
| 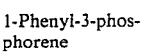 | 1-Phenyl-3-phosphorene |
| 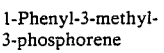 | 1-Phenyl-3-methyl-3-phosphorene |
| 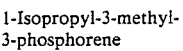 | 1-Isopropyl-3-methyl-3-phosphorene |
| Ph₂—P—(CH₂)₂—P—PH₂ | 1,2-bis(diphenyl-phosphino)ethane |
| Ph₂—P—(CH₂)₃—P—PH₂ | 1,3-bis(diphenyl-phosphino)propane |
| 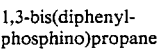 | 2,2'-bis(diphenyl-phosphino)-1,1'-binaphthyl |
| 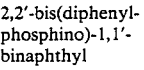 | 2,2'-bis(diparatolyl phosphino)-1,1'-binaphthyl |

The counter anion represented by X in the formula (I) includes, for example, ClO₄⁻, BF₄⁻, PF₉⁻, SiF₆⁻, and B(C₆H₅)₄⁻.

These palladium-phosphine-cation complexes may be prepared according to the process disclosed in Japanese Patent Application (No. 131510/1982) filed by Applicants. More specifically, they are prepared by reacting di-μ-chloro-bis(η-allyl)dipalladium (prepared according to the process described in "Shin-Jikken Kagaku Koza" (New Chemical Experiments), Vol. 12, p. 240) and a methylene chloride solution of the tertiary phosphine of formula (II) or (III) with a perchloride salt, borofluoride salt, hexafluorophosphate salt, hexachlorophosphate salt, or the like of Na, K, Li, or Mg and a quaternary ammonium salt such as triethylbenzylammonium bromide.

Hydroxygeranyl dialkylamine or hydroxyneryl dialkylamine used as the raw material in this invention can be prepared by reacting a secondary amine with nyrcene to give an N-geranylamine derivative [T. Fuzita, K. Suga; Chem. & Ind., p. 231 (1973)] or by reacting a secondary amine with isoprene to give an N-nerylamine derivative [Japanese Patent Publication No.

37537/1980] followed by hydrolyzing the reaction product with a dilute acid according to the process described in *Tetrahedron Letters*, No. 34, pp. 3005–3006 (1975). The alkyl in the dialkylamine may be any lower alkyl group, wherein ethyl and methyl are common.

The deamination reaction of the process for the present invention is represented in the following reaction scheme.

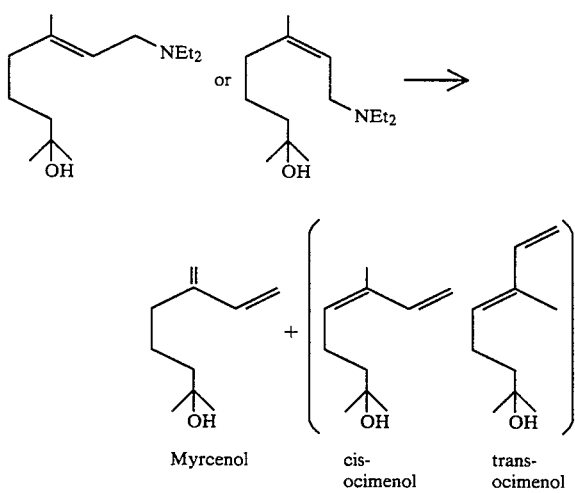

In the deamination reaction, the resulting diene compound should preferably be discharged from the reaction system immediately, and this discharge should preferably be performed by using a distillation column having the number of theoretical plates sufficient for the separation of the raw material compound and the reaction product. The reactor is charged with the raw material compound followed by the addition of 1/400 to 1/2000 mol (based on the raw material compound) of the palladium-phosphine-cation complex as catalyst. The reaction is carried out at a temperature of about 100° to about 150° C. under a reduced pressure of about 1 to about 50 mmHg. The concentration of the catalyst represents the concentration in the reaction system. In the case of a semi-continuous reaction system, the catalyst should be used in an amount of 1/7000 to 1/10,000 based on the total quantity of raw materials charged.

With the deamination reaction, myrcenol, as the main product is distilled away together with ocimenol as a by-product. Upon vacuum distillation of the distillate, the desired myrcenol can be separated and purified.

As previously discussed, the process of this invention makes it possible to produce in one step myrcenol from inexpensive hydroxygeranyl dialkylamine or hydroxyneryl dialkylamine. Ocimenol obtained as a by-product can be used as a raw material for the synthesis of perfumes. Thus the process of this invention is extremely economical from the industrial point of view.

The following non-limiting Examples are afforded in order that those skilled in the art may more readily understand the present invention and specific preferred embodiments thereof with respect to the process of the present invention in accordance with the foregoing description.

EXAMPLE A

This Example illustrates the preparation of a catalyst species to be used in the working Examples.

Into a 500-ml egg-plant type flask equipped with a three-way cock were charged 1.29 g (3.524 mmol) of di-μ-chloro-bis(η-allyl)dipalladium and 3.603 g (8,458 mmol) of 1,4-bis(diphenylphosphino)-butane (referred to as 1,4-Diphos hereinafter). The atmosphere was replaced with nitrogen. Under the nitrogen stream, 130 ml of methylene chloride was added to give a uniform solution. To this solution was further added 211 ml of an aqueous solution (0.1 mol/liter) of sodium fluoride and 35 ml of an aqueous solution (0.02 mol/liter) of triethyl-benzyl-ammonium bromide. The reactants were stirred at room temperature for 2 hours. After the completion of the reaction, the flask was allowed to stand, and the aqueous layer was removed. Thus there was obtained a methylene chloride solution of a complex represented by [<•: Pd•1,4-Diphos]+BF$_4^-$. This catalyst may be used as such (in the form of solution) for the deamination reaction.

The structure of this catalyst was confirmed by NMR spectrum and elemental analysis of white crystals obtained by vacuum drying of the methylene chloride solution.

(1) NMR spectrum:

| | | |
|---|---|---|
| 1.8 ppm | 4 H | —CH$_2$—CH$_2$— |
| 2.6 ppm | 4 H | P—CH$_2$— |
| 3.1 ppm | 2 H | (a) |
| 4.1 ppm | 2 H | (b) |
| 5.7 ppm | 1 H | (c) |
| 7.58 ppm | 20 H | phenyl group |

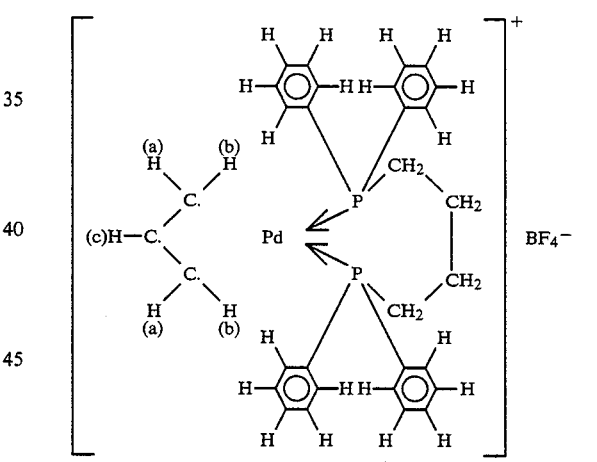

(2) Elemental analysis: C$_{31}$H$_{33}$PdP$_2$BF$_4$: Calculated (%): C 56.35, H 5.03, P 9.37; Found (%): C 56.5, H 5.1, P 9.21

EXAMPLE 1

Into a 1-liter distillation flask equipped with a distillation column (50 mm in diameter, 1 m high, filled with McMahon packing, and the number of theoretical plates of about 4) was charged 400 g of hydroxygeranyl diethylamine (1.762 mol). The atmosphere was replaced with nitrogen. Into the flask was further added 130.5 ml (3.524 mmol) of methylene chloride solution of [<•: Pd•1,4-Diphos]+BF$_4^-$ prepared in the Example A. The reactants were heated under a reduced pressure of 20 mmHg. About 15 minutes after the reaction temperature in the flask had reached 130° C., a mixture of myrcenol and ocimenol was distilled away at a column top temperature of 96° C. and at a reflux ratio of 1:2. IN proportion with the quantity of distillate, hydroxygeranyl diethylmaine was added continuously. During the eaction, which was carried out for over 44 hours, 6.204 kg (27.33 mol) of hydroxygeranyl diethylamine was added, and a mixture of myrcenol and ocimenol was obtained. After rectification, there was obtained 4.09 kg (25.56 mol) of distillate.

The results from gas chromatography indicted that the distillate was a mixture composed of 70% of myrcenol and 30% of ocimenol, and the theoretical yield was 91.3%. The mixture was separated into myrcenol and ocimenol by fractional distillation. Their IR spectrums, NMR spectrums, and mass spectrums coincided with those of respective standard products.

EXAMPLE 2

Example 1 was repeated except that hydroxyneryl diethylamine was used as a raw material. After reaction for 46 hours, there was distilled away 3.96 kg (25.71 mol) of a mixture of myrcenol and ocimenol.

The results from gas chromatography indicated that the distillate was a mixture composed of 66% of myrcenol and 34% of ocimenol, and the theoretical yield was 88.4%.

EXAMPLE 3

Into a 300-ml flask were charged 1.29 g (3.524 mmol) di-μ-chloro-bis(η-allyl)dipalladium and 3.603 g (8.458 mmol) of 1,4-Diphos. Under a nitrogen stream, 1.30 ml of methylene chloride, 2.59 g (21.14 mmol) of sodium perchlorate, and 0.1664 g (0.7 mmol) of triethylbenzylammonium bromide were introduced. The reaction was carried out at room temperature for 2 hours. After the completion of the reaction, the solids were filtered off to give a methylene chloride solution of [<•: Pd•1,4-Diphos]+ClO4− complex. The structure of the catalyst was confirmed by elemental analysis in the same manner as in Example 1.

Elemental analysis for $C_{31}H_{33}PdP_2ClO_4$: Calculated: C 55.29, H 4.94, P 9.19; Found: C 55.4, H 4.83, P 9.3

Into a 300-ml reactor equipped with a rectifying column (with an estimated number of theoretical plates of 10) filled with "Helipack" was charged 103 g (0.454 mol) of hydroxygeranyl diethylamine. The atmosphere was replaced with nitrogen. 33.6 ml (0.908 mmol) of the above-mentioned methylene chloride solution was added, and the reactants were heated under a reduced pressure of 1 mmHg. About 35 minutes after the reactant temperature in the flask had reached 150° C., distillation was started at a column top temperature of 63° C. After carrying out the reaction for 5 hours, a mixture of myrcenol and ocimenol was obtained in an amount of 59.4 g. The results from gas chromatography indicated that the mixture was composed of 87.6% of myrcenol and 12.4% of ocimenol.

EXAMPLES 4 TO 15

Experiments were carried out in the same way as in Example 3 by using the catalyst prepared in Example A. The results are shown in Table 1.

In Examples 4 to 14, the raw material was hydroxygeranyl diethylamine.

In Example 15, the raw material was hydroxyneryl diethylamine.

In Table 1:
1,2-Diphos denotes 1,2-bis(dipehnylphospino)-ethane,
1,3-Diphos denotes 1,3-bis(diphenylphosphino)-propane,
1,4-Diphos denotes 1,4-bis(diphenylphosphino)-butane,
1,6-Diphos denotes 1,6-bis(dipehnylphosphino)-hexane, and BINAP denotes 2,2'-bis(diphenylphosphino)-1,1'-binaphthyl.

TABLE 1

| Example No. | Tertiary phosphine | Counter anion | Yield | Ratio of myrcenol to ocimenol | Concentration of catalyst | Reaction temperature (°C.) | Reaction time (h) |
| --- | --- | --- | --- | --- | --- | --- | --- |
| 4 | 1,2-Diphos | ClO4 | 51.8 | 84:16 | 1/2000 | 150 | 5 |
| 5 | 1,3-Diphos | ClO4 | 47.4 | 86.9:13.1 | 1/2000 | 150 | 5 |
| 6 | 1,4-Diphos | PF6 | 58.4 | 84.6:15.4 | 1/2000 | 150 | 5 |
| 7 | 1,4-Diphos | SiF6 | 20.4 | 47.1:52.9 | 1/2000 | 150 | 5 |
| 8 | 1,6-Diphos | B(C6H5)4 | 16.3 | 80.7:12.3 | 1/2000 | 150 | 5 |
| 9 | ⬡-PPh2 / ⬡-PPh2 | BF4 | 30.0 | 85:15 | 1/2000 | 150 | 5 |
| 10 | BINAP | PF6 | 31.4 | 96:4 | 1/2000 | 130 | 3 |
| 11 | ⬡-PPh | BF6 | 30.6 | 88:12 | 1/2000 | 150 | 5 |
| 12 | PPh3 | ClO4 | 29.0 | 87.7:12.3 | 1/2000 | 150 | 5 |
| 13 | (C4H9)3P | BF4 | 26.4 | 80:20 | 1/2000 | 150 | 5 |
| 14 | (⬡-)3P | BF4 | 22.3 | 70:30 | 1/2000 | 150 | 5 |
| 15 | 1,3-Diphos | ClO4 | 63.7 | 76.5:23.5 | 1/400 | 150 | 4 |

While the invention has been described and illustrated with reference to certain preferred embodiments thereof, those skilled in the art will appreciate that various changes, modifications and substitutions can be made therein without departure from the spirit of the invention. For example, temperature ranges and feed ratios other than the preferred range may be applicable as a consequence of the nature of various reactants employed in the process and such other expected variations or differences in results are contemplated in accordance with the objects and practices of the present invention. It is intended, therefore, that the invention be limited only by the scope of the claims which follow.

What is claimed as new and is desired to be secured by Letters Patent of the United States is:

1. A process for producing myrcenol which comprises:

(a) deaminating hydroxygeranyl dialkylamine or hydroxyneryl dialkylamine with a palladium-phosphine-cation complex catalyst of the formula:

(<•: PdL)⁺X⁻ wherein

<• represents η-allyl,

L represents a tertiary phosphine, and

X represents a counter anion;

said deaminating being carried out at a temperature of about 100°–150° C. and under a reduced pressure of about 1–50 mmHg.

2. The process according to claim 1, wherein the tertiary phosphine is composed of two monodentate ligands of the formula:

wherein $R_1$, $R_2$, and $R_3$ are the same or different and represent lower alkyl, cycloalkyl, or aryl; and $R_2$ and $R_3$ may jointly form a five-membered ring with the adjoining carbon atoms.

3. The process according to claim 1, wherein the tertiary phosphine is a bidentate ligand of the formula:

(R)₂—P—Y—P—(R)₂ wherein

R represents lower alkyl, cycloalkyl, or aryl; and

Y represents

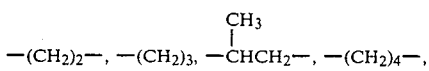

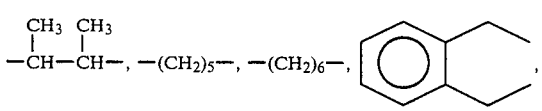

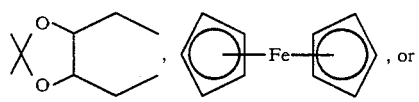

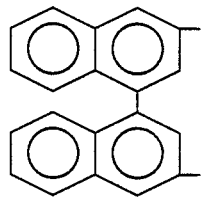

, or

4. The process according to claim 1, wherein the counter anion is $ClO_4^-$, $BF_4^-$, $PF_6^-$, $SiF_6^-$, or $B(C_6H_5)_4^-$.

5. The process according to claim 1, wherein said deamination is carried out at a temperature that range from about 100° C. to about 150° C. and at a reduced pressure that ranges from about 1 mmHg to about 50 mmHg.

6. The process according to claim 1, wherein the concentration of said catalyst may range from about 1/400 to about 1/10,000 based on the raw material compound.

7. The process of claim 1, wherein the palladium-phosphine-cation complex is added in amount about 1/400 to 1/2,000 mol. based on the dialkylamine.

8. The process of claim 1, wherein the the catalyst is used in an amount of about 1/7,000 to 1/10,000 based on the total quantity of the dialkyamine for a semi-continuous reaction system.

9. The process of claim 1, further comprising:

(b) separating the myrcenol from the remaining components of the reaction mixture by distillation.

10. The process of claim 9, further comprising:

(c) distilling under vacuum the product of step (b).

* * * * *

UNITED STATES PATENT AND TRADEMARK OFFICE
CERTIFICATE OF CORRECTION

PATENT NO. : 4,520,212  
DATED : May 28, 1985  
INVENTOR(S) : Mitsuhashi, Shigeru; Kumobayashi, Hidenori; and Akutagawa, Susumu Page 1 of 3

It is certified that error appears in the above-identified patent and that said Letters Patent is hereby corrected as shown below:

Column 1, line 9, delete "hydroxynerin" and insert therefor: --hydroxyneryl--.

Column 1, line 35, delete "pyrolyzine" and insert therefor: --pyrolyze--.

Column 4, structures 5 and 6, delete "-PH$_2$" and insert therefor: ---Ph$_2$--.

Column 3, names of structures 3,4,5, delete "isopropylydene" and insert therefor: --isopropylidene--.

Column 3, name of structure 4, delete "bis(dicyclohexyl-" and insert therefor: --bis(diphenyl---.

Column 4, line 46, delete "aninon" and insert therefor: --anion--.

Column 4, line 47, delete "PF$_9$" and insert therefor: --PF$_6$--.

Column 4, line 64, delete "nyrcene" and insert therefor: --myrcene--.

UNITED STATES PATENT AND TRADEMARK OFFICE
CERTIFICATE OF CORRECTION

PATENT NO.  : 4,520,212

DATED       : May 28, 1985

INVENTOR(S) : Mitsuhashi, Shigeru; Kumobayashi, Hidenori; and Akutagawa, Susumu

It is certified that error appears in the above-identified patent and that said Letters Patent is hereby corrected as shown below:

Column 5, line 1, delete "hydrolyzing" and insert therefor: --hydrating--.

Column 5, line 50, delete "vacuum" and insert therefor: --fractional--.

Column 6, line 9, delete "fluoride" and insert therefor: --borofluoride--.

Column 6, line 68, delete "IN" and insert therefor: --In--.

Column 7, line 3, delete "eaction" and insert therefor: --reaction--.

Column 7, line 6, delete "rectification" and insert therefor: --redistillation--.

Column 7, line 29, delete "1.30" and insert therefor: --130--.

Column 7, line 64, delete "1" and insert therefor: --A--.

UNITED STATES PATENT AND TRADEMARK OFFICE
CERTIFICATE OF CORRECTION

PATENT NO. : 4,520,212

DATED : May 28, 1985

INVENTOR(S) : Mitsuhashi, Shigeru; Kumobayashi, Hidenori; and Akutagawa, Susumu

It is certified that error appears in the above-identified patent and that said Letters Patent is hereby corrected as shown below:

Column 8, line 24, delete "(dipehnylphospino)" and insert therefor: --(diphenylphosphino)--.

Column 8, line 28, delete "(dipehnyl" and insert therefor: --(diphenyl--.

Signed and Sealed this

Twenty-sixth Day of November 1985

[SEAL]

Attest:

DONALD J. QUIGG

Attesting Officer     Commissioner of Patents and Trademarks